United States Patent
Henke et al.

(10) Patent No.: US 12,214,149 B2
(45) Date of Patent: Feb. 4, 2025

(54) APPLICATOR SYSTEM CONTAINING A MICRONEEDLE ARRAY WHICH COMPRISES AN ACTIVE INGREDIENT FOR WOUND HEALING

(71) Applicant: LTS LOHMANN THERAPIE-SYSTEME AG, Andernach (DE)

(72) Inventors: Stefan Henke, Kirchen (DE); Karsten Heuser, Bad Breisig (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 568 days.

(21) Appl. No.: 16/634,592

(22) PCT Filed: Aug. 4, 2018

(86) PCT No.: PCT/EP2018/071209
§ 371 (c)(1),
(2) Date: Jan. 28, 2020

(87) PCT Pub. No.: WO2019/025625
PCT Pub. Date: Feb. 7, 2019

(65) Prior Publication Data
US 2020/0188649 A1   Jun. 18, 2020

(30) Foreign Application Priority Data
Aug. 4, 2017   (DE) ...................... 10 2017 117784.1

(51) Int. Cl.
| A61M 37/00 | (2006.01) |
|---|---|
| A61K 9/00 | (2006.01) |
| A61K 31/164 | (2006.01) |
| A61K 31/17 | (2006.01) |
| A61K 31/728 | (2006.01) |
| A61K 36/63 | (2006.01) |
| A61K 36/886 | (2006.01) |
| A61K 38/39 | (2006.01) |

(52) U.S. Cl.
CPC ....... *A61M 37/0015* (2013.01); *A61K 9/0021* (2013.01); *A61K 31/164* (2013.01); *A61K 31/17* (2013.01); *A61K 31/728* (2013.01); *A61K 36/63* (2013.01); *A61K 36/886* (2013.01); *A61K 38/39* (2013.01); *A61M 2037/0023* (2013.01)

(58) Field of Classification Search
None
See application file for complete search history.

(56) References Cited

U.S. PATENT DOCUMENTS

| 3,964,482 | A | * | 6/1976 | Gerstel | A61M 37/0015 |
|---|---|---|---|---|---|
| | | | | | 604/890.1 |
| 6,611,707 | B1 | * | 8/2003 | Prausnitz | A61M 37/0015 |
| | | | | | 604/21 |
| 2002/0128599 | A1 | * | 9/2002 | Cormier | A61M 37/0015 |
| | | | | | 604/116 |
| 2005/0203575 | A1 | | 9/2005 | Carson et al. | |
| 2007/0066934 | A1 | * | 3/2007 | Etheredge, III | A61M 37/0015 |
| | | | | | 604/173 |
| 2007/0081977 | A1 | | 4/2007 | Horstmann | |
| 2011/0319865 | A1 | | 12/2011 | Buss | |
| 2014/0066843 | A1 | * | 3/2014 | Zhang | A61P 23/02 |
| | | | | | 604/512 |
| 2014/0276366 | A1 | | 9/2014 | Bourne et al. | |
| 2015/0057604 | A1 | * | 2/2015 | Arami | A61M 37/0015 |
| | | | | | 29/428 |
| 2017/0050010 | A1 | | 2/2017 | McAllister et al. | |
| 2018/0099133 | A1 | | 4/2018 | Heuser et al. | |

FOREIGN PATENT DOCUMENTS

| DE | 10353629 | A1 | 6/2005 |
|---|---|---|---|
| EP | 2578264 | A1 | 4/2013 |
| EP | 2835147 | A1 | 2/2015 |
| WO | WO-2008053481 | A1 | 5/2008 |
| WO | WO-2008091602 | A2 | 7/2008 |
| WO | 2013/151044 | A1 | 10/2013 |
| WO | WO-2016162449 | A1 | 10/2016 |

OTHER PUBLICATIONS

International Preliminary Examination Report for PCT/EP2018/071209 mailed Nov. 8, 2019.
International Search Report for PCT/EP2018/071209 mailed Nov. 22, 2018.
Written Opinion of the International Searching Authority for PCT/EP2018/071209 mailed Nov. 22, 2018.

* cited by examiner

*Primary Examiner* — Bethany P Barham
*Assistant Examiner* — Peter Anthopolos
(74) *Attorney, Agent, or Firm* — Faegre Drinker Biddle & Reath LLP

(57) ABSTRACT

The invention relates to an applicator system comprising a microneedle array and to the use thereof for the intradermal delivery of active ingredients, and in particular of medicinal drugs, wherein this microneedle array is suitable for penetrating the skin of humans or animals and includes at least one active ingredient for wound healing.

12 Claims, No Drawings

APPLICATOR SYSTEM CONTAINING A MICRONEEDLE ARRAY WHICH COMPRISES AN ACTIVE INGREDIENT FOR WOUND HEALING

CROSS-REFERENCE TO RELATED APPLICATIONS

This application is a national stage application (under 35 U.S.C. § 371) of PCT/EP2018/071209, filed Aug. 4, 2018, which claims benefit of German Application No. 10 2017 117784.1, filed Aug. 4, 2017, both of which are incorporated herein by reference in their entirety.

The invention relates to an applicator system comprising a microneedle array and to the use thereof for the intradermal delivery of active ingredients, and in particular of medicinal drugs, wherein this microneedle array is suitable for penetrating the skin of humans or animals and includes at least one active ingredient for wound healing.

Microneedle systems and devices in which microneedle arrays are used for the painless intradermal (or transdermal) administration of substances, and in particular of medicinal drugs, are known from the prior art. Nonetheless, there is a high need to promote wound healing.

The skin consists of several layers. The outermost layer of the skin, this being the stratum corneum, has known barrier properties to prevent foreign substances from penetrating into the body and the body's own substances from exiting the body. The stratum corneum, which is a complex structure composed of compacted horny cell residues having a thickness of approximately 10 to 30 micrometers, forms a watertight membrane for this purpose to protect the body. This natural impermeability of the stratum corneum prevents most pharmaceutical agents and other substances from being administered through the skin as part of an intradermal delivery.

As a result, various substances are therefore administered, for example, by generating micropores or cuts in the stratum corneum and feeding or delivering a medicinal drug into or beneath the stratum corneum. In this way, it is also possible to administer a number of medicinal drugs subcutaneously or intradermally or intracutaneously, for example.

In the prior art, a problem that continues to exist is that wound healing takes place with delay since micropores and cuts are located closely next to one another when a microneedle array is used and impair wound healing. This delay allows bacteria and other invading microbes to penetrate into the skin and, in the worst-case scenario, to trigger inflammations and even infections.

In the prior art, US 2011/319865 describes a microneedle device, however for cosmetic use, wherein healing substances are also delivered by way of a so-called "roller." Such a roller, however, is not an applicator system comprising a microneedle array for the administration of active ingredients.

In particular, applicator systems are used to place a microneedle array onto the skin under pressure and result in a sudden burden on the skin. The strong brief pressure burden on the skin can result in additional irritation and microlesions, or even (micro) skin tears. This problem can be accompanied by the symptom of considerable itching, with reddening of the skin and swelling of the skin.

The object for an applicator system comprising a microneedle array for the intradermal delivery of active ingredients, and in particular medicinal drugs, is thus to promote wound healing during and after the delivery, and to prevent negative sequelae such as itching, swelling, skin irritations, redness, blisters, bleeding and inflammation.

The object is achieved by the conveyed technical teaching of the claims.

The invention thus relates to such a teaching, in particular having the features of claim 1, this being an applicator system comprising a microneedle array for use with the intradermal delivery of a first active ingredient, comprising a plurality of microneedles on a carrier, wherein the microneedles and/or the carrier comprise at least one second active ingredient for wound healing.

According to the invention, such suitable active ingredients for wound healing are selected from the group consisting of absinthe, algae extract, allantoin, allantoinum, Allium cepa, Aloe vera, aluminum acetate, ammonium bituminosulfonate, pineapple extract, apricot kernel oil, argan oil, arnica, eyebright extract, bamboo extract, benzalkonium chloride, benzethonium chloride, beta carotene, beeswax, henbane oil, bismuth, broccoli seed oil, calendula, cetylpyridinium chloride, chondroitin, citronella, caffeine, collagen, cupuacu butter, dexpanthenol, dextrocamphora, guaiacum, pomegranate extract, witch hazel bark, hemodialysates, urea, helianthus oil, hyaluronic acid, jojoba oil, chamomile flowers, kaolin, common poppy, Venice turpentine, lavandula, cod liver oil, levomenol, lidocaine, hollyhock, almond oil, macrogol, myrrh, myrrh resin extract, sodium hyaluronate, olive oil, oxyquinoline, pantothenic acid, Peru balsam, phenyl salicylate, pine resin, polidocanol, pyolysin, resorcinol, castor oil, rosemary, samphire, sea buckthorn oil, yarrow, sesame oil, shea butter, benzoin Siam, soy isoflavones, soy bean oil, sunflower oil, coneflower, spike oil, thymol, Tolu balsam, tormentil root stock, grapeseed oil, tyrothricin, Vitamin A, Vitamin E (tocopherol), frankincense, wheat germ oil, witch hazel (hamamelis), zinc oxide, and onion extract (*Allium cepa*).

Active ingredients that, additionally, have a nourishing effect for the skin, such as dexpanthenol, collagen and hyaluronic acid, are particularly preferred. Furthermore, *Aloe vera*, olive oil and urea are preferred.

Furthermore, the active ingredient for wound healing can be incorporated into a formulation comprising customary additives and auxiliary substances, and in particular into a liquid or a gel.

Furthermore, the first active ingredient, such as a medicinal drug, is to be different from the second active ingredient for wound healing.

According to the invention, the term "wound healing" encompasses physiological processes for the regeneration of destroyed skin tissue (epidermis, dermis), which cause wound closure, in particular by the formation of new connective tissue or capillaries. Within the scope of the present invention, a distinction is to be made between primary wound healing with rapid, uncomplicated wound closure as a result of minimal new connective tissue formation between, possibly adapted, margins of a clean wound that are supplied well with blood, and secondary wound healing with delayed wound healing as a result of an inevitable bacterial inflammation in the case of wounds having a multitude of margins, or wound infection with the tissue defect being filled in with granulation tissue and extended scarring and epithelialization, starting from the margin.

Moreover, the phases of the wound healing process are noteworthy, these being the latency phase where liquid oozes and scabs form during the initial hours and a resorptive phase with catabolic autolysis where damaged tissue is broken down. These are followed by the proliferative phase or granulation phase with anabolic repair, with collagen being formed by connective tissue cells (fibroblasts), and finally a repair phase where the granulation tissue is converted into scar tissue. What is essential now is that the active ingredients for wound healing are able to support the wound healing process, optionally to support the aforementioned phases, and to avoid complications on and in the wound.

Within the scope of the present invention, an applicator system is a system comprising a device that causes the microneedle array for administering the active ingredients onto the skin to be provided, and the first and second active ingredients for wound healing to be intradermally delivered.

In a preferred embodiment, the applicator system can comprise a trigger device, which is electrically or mechanically controlled. For example, the applicator system can comprise a plunger, which places or applies the microneedle array onto the skin, so that the microneedles penetrate the skin.

The trigger device can comprise a pump, a syringe or a spring, for example, whereby a push of the plunger can be carried out with sufficient energy. The plunger can be of any arbitrary, shape and nature and is to primarily achieve that the microneedle array is provided from a first position into a second position for administering the active ingredients onto the skin.

The applicator system can furthermore comprise a push button or a thread. Furthermore, the applicator system can be designed in such a way that the first active ingredient is released, for example by the opening of an active ingredient reservoir.

The microneedle array can comprise a plurality of microneedles so as to be able to release a substance via the skin or into the skin of a patient, wherein the microneedle array is placed onto the skin of the patient. Each of the microneedles of the microneedle array preferably comprises an elongated shaft having two ends, the one end of the shaft forming the base of the microneedle by way of which the microneedle is attached to the planar carrier or by way of which the microneedle is integrated into the planar carrier. The end of the shaft located opposite the base preferably has a tapered shape so as to enable the microneedle to penetrate into the skin as easily as possible. Each hollow microneedle includes at least one passage or channel or at least one borehole, which extends from the base of the microneedle to the tip of the microneedle or approximately to the tip of the microneedle. The passages preferably have a round diameter.

The microneedles can be produced from a variety of materials and are made, for example, of a metal, a ceramic material, a semiconductor, an organic material, a polymer or a composite, each having a solid or semi-solid or hollow design.

Preferred materials for producing such microneedles are, for example, pharmaceutically acceptable stainless steel, steel, gold, titanium, nickel, iron, tin, chromium, copper, palladium, platinum, alloys of the aforementioned metals, silicon, silicon dioxide, glass, plastics and polymers. The polymers can particularly preferably include biodegradable polymers or water-soluble polymers, in particular of biological or non-biological origin, preferably polymers such as alpha-hydroxy acids, such as lactic acid and/or glycolic acid, polylactides, polyglycolides, polylactide-co-glycolides, and copolymers with polyethylene glycol, polyanhydrides, poly(ortho)esters, polyurethanes, polybutyric acids, polyvaleric acids, and polylactide-co-caprolactones. The polymers can likewise be non-biodegradable polymers, for example, from the group of the polycarbonates, polyesters, polyvinyl chloride, polyacrylamides, cycloolefin (co)polymers, polymethacrylates and thermoplastics. In another embodiment, the microneedles are made of a monocrystalline material, such as monocrystalline silicon.

The microneedles can comprise a shaft having a round cross-section or a non-round cross-section, for example having a triangular, quadrangular or polygonal cross-section. The shaft can have one passage or multiple passages, extending from the needle base to the needle tip or approximately to the needle tip. The microneedles can be designed as (barbed) hooks, wherein one or more of these microneedles comprise one or more of such hooks. Furthermore, the microneedles can be configured in a helical shape and be rotatably disposed and thereby, when a rotating motion is applied, facilitate penetration into the skin and effectuate anchoring in the skin (DE 103 53 629 A1), in particular at the desired penetration depth in the epidermis.

The diameter of a microneedle typically ranges between 1 µm and 1000 µm, and preferably between 10 µm and 100 µm. The diameter of a passage typically ranges between 3 µm and 80 µm and is suitable for preferably liquid substances, solutions and substance preparations to pass through. The length a microneedle typically ranges between 5 µm and 6,000 µm, and in particular between 100 µm and 700 µm.

The microneedles are attached at the base thereof to a planar carrier or are integrated into a planar carrier. The microneedles are preferably disposed so as to be situated substantially perpendicularly to the surface area of the carrier. The microneedles can be arranged regularly or irregularly. An arrangement of multiple microneedles can comprise microneedles having differing cross-sectional shapes, differently dimensioned diameters and/or differing lengths. The arrangement of multiple microneedles can exclusively comprise hollow microneedles, for example. The arrangement can likewise comprise solid microneedles as well as semi-solid composites, such as solid microneedles interspersed with liquid inclusions.

The density of the microneedles on a carrier is 5 to 5,000 pieces/cm$^2$, and in particular 5 to 1,000 pieces/cm$^2$. In particular, high densities of microneedles can impair wound healing.

The microneedle array can comprise a planar carrier, wherein the carrier essentially has a disk-shaped, plate-shaped or film-shaped basic shape. The carrier can have a round, an oval, a triangular, a quadrangular or a polygonal base surface area. The carrier can be produced from a variety of materials, such as a metal, a ceramic material, a semiconductor, an organic material, a polymer or a composite. Materials suitable for producing the carrier can preferably be films or web-shaped materials, for example microporous membranes, preferably made of polyethylene (PE) or polypropylene (PP), or diffusion membranes, preferably made of ethylene-vinyl acetate copolymer (EVA) or polyurethane (PUR). Suitable materials for producing the carrier can be selected from the group consisting of polyesters, such as polyethylene terephthalates (PET), polycarbonates (PC), polyether ketones (PAEK) polyethylene naphthalate (PEN), polybutylene terephthalates (PBT), polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA), polymethyl methacrylate (PMMA) and cellulose-based plastic materials, such as cellulose hydrate or cellulose acetate. Suitable materials for producing the carrier can also be selected from the group of metals, which include aluminum, iron, copper, gold, silver, platinum, alloys of the aforementioned metals, and other pharmaceutically acceptable metal foils or metallized films.

The carrier is preferably made of a flexible material, for example a plastic material. A carrier made of a flexible material can better conform to the surface of the skin and the curvature thereof than a carrier made of a non-flexible material. In this way, better contact between the microneedle array and the skin is achieved, thereby improving the reliability of the microneedle array.

In a preferred embodiment, the microneedle array is a flat or planar microneedle array.

It is now essential for the invention that such a microneedle array is at least wetted with an active ingredient for wound healing or that preferably an active ingredient for wound healing is included.

In a preferred embodiment, the active ingredient for wound healing can be integrated or incorporated into the matrix of the microarray. In a preferred embodiment, the active ingredient can further be applied onto the microneedles or onto the carrier for wound healing.

In a particularly preferred embodiment, for example, the tip of at least one microneedle is wetted with an active ingredient for wound healing or an active ingredient for wound healing is included in the tip of at least one microneedle.

The active ingredient for wound healing can be present on the and/or in the microneedle array and/or carrier in an amount of 0.01 to 200 mg/cm$^2$.

In a further embodiment, the applicator system comprising a microneedle array can be configured with customary functional objects that allow fixation on the skin as well as easy handling for exerting pressure onto the skin and that can comprise, in particular, at least one fixation means.

The applicator system comprising a microneedle array can comprise at least one reservoir, which contains at least one arbitrary substance, and in particular a first active ingredient or medicinal drug, preferably in the form of a solution or preparation.

The reservoir is used to store the at least one arbitrary active ingredient or medicinal drug included in the system.

The reservoir is connection to the passages of the hollow microneedles in such a way that a liquid connection exists between the reservoir and the passages of the microneedles connected to the reservoir. In this way, the content of the reservoir can be released from the reservoir via the passages of the microneedles out of the microneedle system when pressure is exerted onto the reservoir after the microneedle system has been placed onto the skin. The preparation on hand exits the microneedle system at or in the vicinity of the tips of the microneedles and can penetrate into the target tissue. The reservoir is usually attached to a surface of the planar carrier, this being the surface of the carrier located opposite the surface of the carrier from which the microneedles project.

The reservoir is easy to compress so as to offer little resistance to the pressure exerted onto the reservoir, and thereby be able to pass the pressure onto the preparation contained in the reservoir for the same to exit. According to one embodiment, the reservoir can be present in the form of a flexible bag, for example.

According to a preferred embodiment, the reservoir is designed as a pad or a balloon and produced from elastic material, for example from an elastomeric polymer or rubber. Examples of polymers include polyesters, such as polyethylene terephthalates (PET), polycarbonates (PC), polyether ketones (PAEK), polyethylene naphthalate (PEN), polybutylene terephthalates (PBT), the polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA) and cellulose-based plastic materials, such as cellulose hydrate or cellulose acetate.

In another preferred embodiment, the microneedle system comprising a microneedle array is configured with an applicator. Such applicators advantageously allow a pressure mechanism to be activated for the microneedle array to penetrate the skin or stratum corneum (see, for example, WO2008091602A2, WO2016162449A1).

According to a further embodiment, the microneedle array can comprise fixation means that are preferably attached to the skin of a patient or test subject by way of a contact adhesive strip or patch. Suitable contact adhesives include high viscosity substances that adhere to the skin after briefly applying minor pressure, known as pressure-sensitive adhesives (PSA). These have high cohesion and adhesion forces. It is possible, for example, to use poly(meth)acrylate-based, polyisobutylene-based or silicone-based contact adhesives. In a further embodiment, the fixation means can be made up of a band, an elastic band, rubber or strap. Secure fastening to the body can be achieved by way of such fixation means.

The invention thus relates to an applicator system according to the invention, comprising a microneedle array for intradermal delivery, which comprises fixation means for the skin.

According to the invention, the term "intradermal delivery" (synonym: "intracutaneous delivery") describes the administration of arbitrary active ingredients via the microneedle array into the skin and requires the microneedles to pierce or penetrate the skin.

The invention thus likewise relates to a method for intradermal delivery, wherein at least one first active ingredient is delivered by means of an applicator system comprising a microneedle array, comprising a plurality of microneedles on a carrier, wherein the microneedles and/or the carrier include at least one second active ingredient for wound healing.

The following examples are provided to further describe the invention, without limiting the invention to these examples.

EXAMPLE 1 a.) Experimental Design

A microarray without dexpanthenol and a microarray with 150 mg dexpanthenol are each manually applied onto healthy skin (underarm), fixed with tape, and removed after a wearing period of one hour. For comparison, the application site is photographed prior to placing on the microarrays, immediately after removal of the microarrays without wiping off potential residue, and after 70 hours.

b.) Materials and Methods

Microarray Stansomatic Octagon 536; W1.4301
Dexpanthenol Ph. Eur. LOT #BCBQ1802V
Hansaplast Leukosilk fixation tape
Canon EOS 1200D camera c.) Results and Discussion The skin treated with the microarray without dexpanthenol is reddened and injured in some areas. The skin treated with the microarray with dexpanthenol is less reddened. No injuries are visible to the naked eye.

d.) Conclusion

The pretreatment of microarrays with dexpanthenol reduces the undesirable effects that accompany the application.

Similar experiments were carried out for collagen, hyaluronic acid, *Aloe vera*, olive oil and urea. The amounts used range between 0.01 mg and 200 mg/cm$^2$.

In all experiments, the skin is less reddened, and injuries can be avoided.

The invention claimed is:

1. An applicator system comprising a microneedle array for use for the intradermal delivery of a first active ingredient, the applicator system comprising:
    a plurality of microneedles on a carrier, wherein the microneedles are made of a polymer matrix in which at least one second active ingredient for wound healing is integrated or incorporated;
    a trigger mechanism; and
    at least one reservoir for storing the first active ingredient, the reservoir being in connection to the microneedles; and
    wherein the first active ingredient is different from the at least one second active ingredient for wound healing, and the first active ingredient is a medicinal drug;
    wherein the at least one second active ingredient for wound healing is selected from the group consisting of dexpanthenol, collagen, hyaluronic acid, and combinations thereof; and
    wherein the polymer of the polymer matrix is selected from the group consisting of polylactides, polyglycolides, polylactide-co-glycolides, polyanhydrides, poly(ortho)esters, polyurethanes, polybutyric acids, polyvaleric acids, polylactide-co-caprolactones, polycarbonates, polyesters, polyvinyl chloride, polyacrylamides, cycloolefin (co)polymers, polymethacrylates, and thermoplastics.

2. The applicator system according to claim 1, wherein the microneedle array is planar.

3. The applicator system according to claim 1, wherein the density of the microneedles on a carrier is 5 to 5,000 pieces/cm$^2$.

4. The applicator system according to claim 1, wherein the at least one second active ingredient for wound healing is integrated or incorporated in the polymer matrix in an amount of 150 to 200 mg/cm$^2$.

5. The applicator system according to claim 1, wherein the microneedle array comprises fixation means.

6. The applicator system according to claim 1, wherein the microneedle array comprises fixation means which is selected from the group consisting of adhesive strip, patch, band, elastic band, rubber and strap.

7. The applicator system according to claim 1, wherein the first active ingredient is stored in the reservoir.

8. The applicator system according to claim 1, wherein the reservoir is a flexible bag or a balloon.

9. The applicator system according to claim 1, wherein the carrier is flexible and planar and the plurality of microneedles are integrated into the flexible planar carrier.

10. The applicator system according to claim 9, wherein the applicator system comprises at least one reservoir containing the first active ingredient.

11. An applicator system comprising a microneedle array for the intradermal delivery of a first active ingredient, the applicator system comprising:
    a plurality of microneedles on a carrier, wherein the microneedles are made of a polymer matrix in which at least one second active ingredient for wound healing is integrated or incorporated;
    a trigger mechanism; and
    at least one reservoir in connection with the microneedles; and
    wherein the at least one reservoir contains the first active ingredient;
    wherein the first active ingredient is different from the at least one second active ingredient for wound healing, and the first active ingredient is a medicinal drug;
    wherein the at least one second active ingredient for wound healing is selected from the group consisting of dexpanthenol, collagen, hyaluronic acid, and combinations thereof; and
    wherein the polymer of the polymer matrix is selected from the group consisting of polylactides, polyglycolides, polylactide-co-glycolides, polyanhydrides, poly(ortho)esters, polyurethanes, polybutyric acids, polyvaleric acids, polylactide-co-caprolactones, polycarbonates, polyesters, polyvinyl chloride, polyacrylamides, cycloolefin (co)polymers, polymethacrylates, and thermoplastics.

12. The applicator system according to claim 11, wherein the reservoir is a flexible bag or a balloon.

* * * * *